United States Patent [19]

Schulz et al.

[11] Patent Number: 5,722,980
[45] Date of Patent: Mar. 3, 1998

[54] DEVICE FOR REMOVAL OF CALCULI

[75] Inventors: Manfred Schulz, Überlingen; Wolfgang Merkle, Linnich, both of Germany

[73] Assignee: Ferton Holding, Delmont, Switzerland

[21] Appl. No.: 391,502

[22] Filed: Feb. 21, 1995

[30] Foreign Application Priority Data

Feb. 22, 1994 [DE] Germany .................. 44 05 656.7

[51] Int. Cl.$^6$ .................................................. A61B 17/22
[52] U.S. Cl. .................... 606/128; 606/2.5; 604/22
[58] Field of Search .................. 606/128, 2.5, 3, 606/129, 127, 1; 604/22, 27, 35

[56] References Cited

U.S. PATENT DOCUMENTS

| 4,178,935 | 12/1979 | Gekhman et al. ............ 606/128 |
| 4,816,018 | 3/1989 | Parisi .......................... 606/128 |
| 5,160,336 | 11/1992 | Favre . | |
| 5,217,468 | 6/1993 | Clement ...................... 606/127 |
| 5,311,858 | 5/1994 | Adair .......................... 606/127 |

FOREIGN PATENT DOCUMENTS

| 0317507B1 | 5/1989 | European Pat. Off. . |
| 3720424C2 | 12/1987 | Germany . |
| 2268883 | 1/1994 | United Kingdom . |
| WO93/08750 | 5/1993 | WIPO . |

Primary Examiner—Robert A. Hafer
Assistant Examiner—Justine R. Yu
Attorney, Agent, or Firm—Ratner & Prestia

[57] ABSTRACT

A device for removing calculi by using an intracorporeal lithotripter (1) including a probe (2) transmitting impact waves is characterized by a guiding tube (5) for the probe, which is adapted for introduction into the operating passage of an endoscope and which is provided with a suction and/or extraction passage (8, 9, 10, 15) for removal of the calculi fragmented by means of the probe, for connexion to a suction pump.

9 Claims, 2 Drawing Sheets

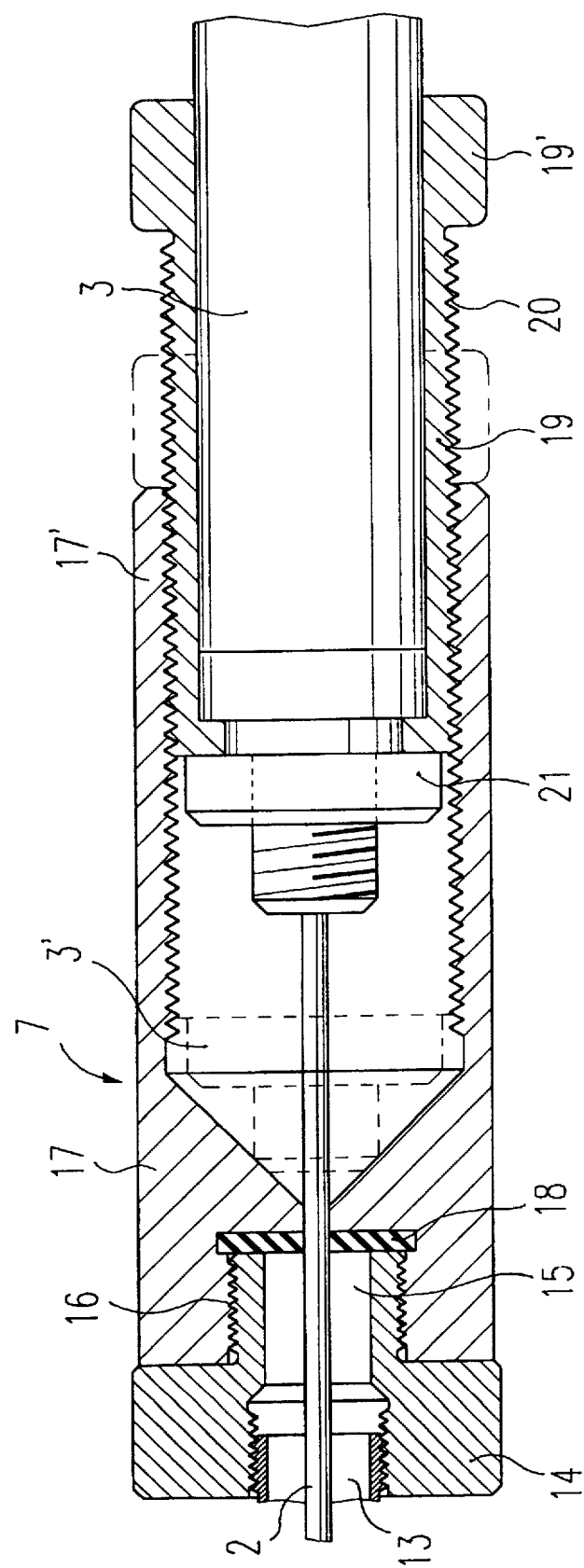
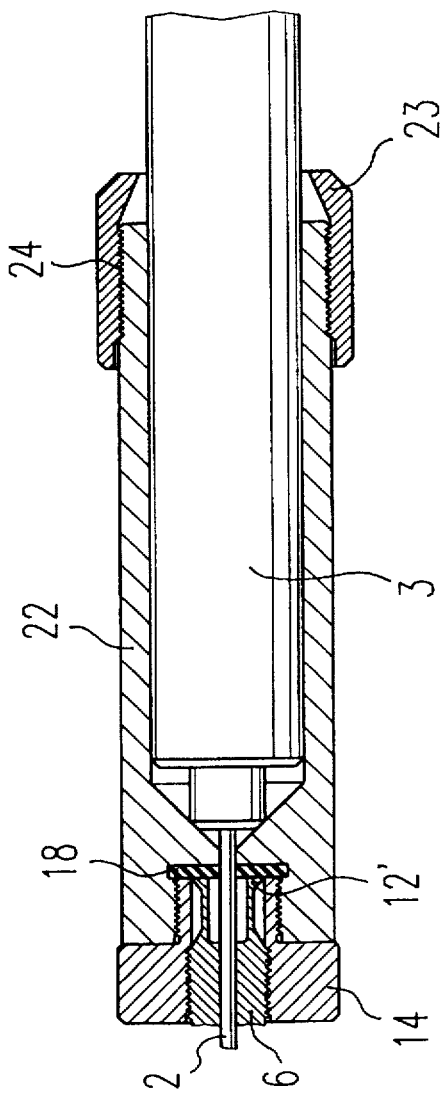
Fig. 2
Fig. 3

DEVICE FOR REMOVAL OF CALCULI

FIELD OF THE INVENTION

The present invention relates to a device for removal of calculi in accordace with the introductory clause of Claim 1.

BACKGROUND OF THE INVENTION

The European Patent EP 0 317 507 B1 discloses a lithotripter wherein impact energy is applied onto a probe transmitting shock waves by means of a pneumatically traversed projectile, which energy causes a calculus to be fragmented when the tip of the probe contacts same. The intracorporeal lithotripsy carried out with such a lithotripter is implemented by using an endoscope into whose operating passage the probe of the lithotripter is introduced by a distance so long that the tip of the probe projects slightly beyond the end of the operating passage so as to allow for a contact of the probe tip with the concrement to be fragmented, which contact must be permanently maintained and visually monitored.

The operation with such intracorporeal lithotripters has so far largely proved to be successful even though it still involves the disadvantage that an optimum lithotripsy requires a permanent corrective adjustment of the relative position of the probe tip with respect to the calculus to be fragmented, so as to be able, even with a decrease of the concrement fragments, to locate their points of attack which offer the least resistance for ensuring a correspondingly optimum lithotripsy result up to a concrement size which the physician can assess to be appropriate for a spontaneous miction, particularly for miction in the case of simultaneous insertion of a splinting catheter. The lithotripsy proper is hence necessarily linked up with this assessment of potential removal of the fragmented concrements by means of an inserted splinting catheter.

The German Patent DE 35 45 176 C2 discloses an endoscope having an operating passage into which either an optical endoscope system combined with retractor means or an optical operating system combined with an ultrasonic sonotrode may be selectively introduced. A receiving pocket made of a ductile rubber-elastic material is attached onto the free end of the operating passage; this pocket presents a receiving opening which may be temporarily resiliently flared by means of the retractor in opposition to the elastic resetting force of the receiving pocket for receiving a calculus to be fragmented. The lithotriptic operation is carried out in the receiving pocket as soon as the retractor means is withdrawn from the operating passage of the endoscope and an ultrasonic sonotrode has been introduced instead into the operating passage. The resiliently reset receiving pocket, which is then closed again at the receiving opening, prevents calculus fragments produced by lithotripsy from being discharged, which fragments may finally, after removal of the sonotrode, be correspondingly safely removed together with the receiving pocket which remains at the operating passage of the endoscope shaft.

The German Patent DE 37 20 424 C2 discloses an ultrasonic sonotrode wherein a flexible vibration transmitting element is provided to transmit the ultrasound waves generated therewith, which is enclosed by a tubular protective sheathing via which a perfusion liquid is supplied, by means of the sonotrode, into the cavity where a concrement is located which is to be fragmented by means of the sonotrode. On the outside of the protective sheathing an annular passage is formed, either in cooperation with an additional plastic tubing or with the surrounding wall of the operating passage of an endoscope; the vibration transmitting element, protected by the protective sheathing, is then introduced into this annular passage which serves for extracting the perfusion liquid and the calculus fragments produced in operation with the sonotrode. At the same time, such an arrangement, in relation to a sonotrode casing adapted to be used as handpiece, is selected for the protective sheathing that a traversing displacement of this protective sheathing relative to the vibration transmitting element allows for exposing the terminal section of this element for fragmentation of a calculus.

SUMMARY OF THE INVENTION

The invention as characterized by the claims now solves the problem of providing a device for removal of calculi, which allows for a less problematic fragmentation of concrements and which renders, at the same time, the removal of the calculus fragments produced in such lithotripsy less critical if an intracorporeal lithotripter is used which presents the aforedescribed configuration and application.

The inventive combination of an intracorporeal lithotripter or its probe transmitting impact waves, respectively, with a guiding tube operating as extraction passage and hence adapted to be introduced together with the probe into the operating passage of an endoscope, ensures, on the one hand, that each target calculus to be fragmented, at which the probe tip aims, may be retained at the free end of the guiding tube under the effect of the suction pressure applied to the extraction passage. The calculus fragments produced during lithotripsy may, on the one hand, be extracted directly through the extraction passage, to which end the annular passage is primarily available and formed between the guiding tube and the lithotripter probe introduced coaxially into this tube. As an alternative the entire lumen of the guiding passage is available for removal of the calculus fragments as soon as the lithotripter has been detached from the guiding tube and the probe has been retracted from the guiding tube.

One embodiment of the inventive device for removal of calculi is schematically illustrated in the drawing and will be described in more details in the following. In the drawing:

BRIEF DESCRIPTION OF THE DRAWINGS

FIG. 2 is a longitudinal section view of the coupler means by means of which an adapter of the guiding tube of the device according to FIG. 1 may be attached to the handpiece of the lithotripter; and FIG. 3 is a longitudinal sectional view of an alternative embodiment of the coupler means.

DESCRIPTION OF THE PREFERRED EMBODIMENTS

Figure 1:
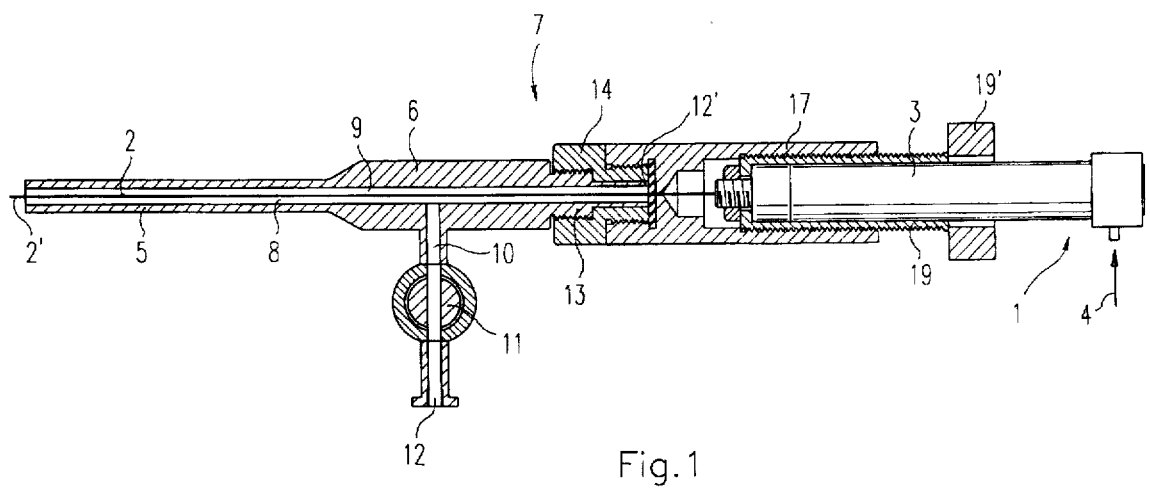
FIG. 1 is an axial sectional view of the device, with a simultaneous illustration of its attachment on the handpiece of a lithotripter, in accordance with a first embodiment.

FIG. 1 is a schematic view of an intracorporeal lithotripter 1 having a probe 2 transmitting impact waves, which presents a configuration in accordance with the European Patent EP 0 317 507 B1 and is manufactured as a so-called "ballistic" lithotripter and distributed by the brand name "Swiss LITHOCLAST" by the company of EMS Electro Medical Systems S. A., Le Sentier (Switzerland). The lithotripter 1 includes a cylindrically shaped handpiece 3 and is provided with a compressed-air fitting 4 for communication with a compressed-air source so that a system is available for driving a projectile moved to and from and serving to transmit impact energy to the probe 2.

The probe 2 is accommodated in a coaxially disposed guiding tube 5 beyond which the probe tip 2' projects in a forward direction so as to permit contact with a calculus to be fragmented, if to this end the guiding tube 5 together with the lithotripter 1, which is fastened on a connector element 6 via a coupler means 7, is introduced into the operating passage of a (non-illustrated) endoscope. The guiding tube 5 is dimensioned so as to form an annular passage 8 between the tube and the probe 2, which annular passage presents an extension in a through-hole 9 of the connector element 6 and is adapted for communication, via a connecting bore 10, ending transversely with respect to the passage, with a suction pump (not illustrated). The annular passage 8 forms a suction passage which when the suction pump is connected retains the calculus at the end of the guiding tube 5 at the outset of the lithotriptic operation so that the impact energy, which is transmitted at the probe tip 2', may be caused to act accurately and selectively onto the calculus. This annular passage 8 equally forms an extraction passage for removal of the calculus fragments having a size smaller than the cross-sectional area of this annular passage 8. The possibility to extract calculus fragments having a maximum diameter up to 2 mm or up to 1.5 mm, when operating with a probe having a diameter of either 1.6 mm or 2 mm, may be quoted as an example in cases where the probe 2 is introduced into a guiding tube 5 of size 12 Fr., a circumferential measure common in endoscopy.

At the connecting bore 10, which communicates with the through-hole 9 of the connector element 6 and which may also be inclined relative to the through-hole in axial alignment with the suction passage of the guiding tube 5, a shut-off element 11 in the form of a so-called trumpet-type valve is disposed by means of which, in case of communication with the suction pump, the suction pressure applied to the suction passage may be adjusted or shut off. For this reason FIG. 1 shows an axially displaceable valve body for the shut-off element 11, which includes a bore which may be aligned with the connecting bore 10. An axial displacement of the valve body controls the fluid communication with a first Luer lock connector 12 which is provided for connexion of the tubing of the suction pump.

The connector element 6 is moreover provided with a thread fitting 13 for screw-fastening thereon a coaxial connecting element 14 of the coupler means 7. As may be more clearly seen in the enlarged view of FIG. 2, this connecting element 14, too, presents a through-hole 15 which forms a second connecting bore for communication with the suction passage of the guiding tube 5 in the axial extension of the through-hole 9 of the connector element 6, and which surrounds a second Luer lock connector 12' provided on the screw fitting When the lithotripter 1 is detached the suction pump tubing connector may be alter-natively connected to the Luer lock connector 12', so that calculus fragments up to a maximum size of 3.5 mm may be extracted through the axial lumen of the guiding tube 5 which is available as extraction passage.

The connecting element 14 of the coupler means 7 is, by the way, provided on an extension having a male thread 16 and surrounding part of the length of the through-hole, onto which thread the connecting end of a coupler sleeve 17, provided with a complementary female thread, may be screwed. A silicone sealing ring 18 is inserted into the connecting end of this coupler sleeve, which ring is fixed on account of the screw engagement with the male thread 16 and seals the extraction passage, formed by the guiding tube 5, from the probe 2 which is passed through the central hole of this sealing ring 18.

The coupler sleeve 17 is connected by friction to the handpiece 3 of the lithotripter, with this friction-type connexion being provided for an axial adjustability of the probe 2 relative to the guiding tube 5 so as to permit adjustment of the extent to which the probe tip 2' projects beyond the end of the guiding tube 5. In the embodiment illustrated in FIG. 2 the friction-type connexion of the coupler sleeve 17 is realized by means of a threaded sleeve 19 which is screwed, for relative adjustment, to an adjusting thread 20 with the fastening end 17' of the coupler sleeve 17. The threaded sleeve 19 is coaxially attached to the handpiece 3 of the lithotripter and retained by means of a nut 21 screwed onto a thread piece of the handpiece so as to prevent axial displacement of the sleeve. When the coupler sleeve 17 and the threaded sleeve 19 are hence rotated relative to each other, with forced rotation of the threaded sleeve 19 on a collar 19', the handpiece 3 of the lithotripter may slidingly axially advance in the coupler sleeve 17 at maximum into the position 3' indicated in dotted lines, in which position the probe tip 2' then axially projects beyond the end of the guiding tube 5 by the longest distance. With the observation of a specified measure of the projection of the probe tip 2' beyond the end of the guiding tube 5 being possibly important in isolated cases, it is expedient to calibrate the the adjusting thread 20 for a specific measure of axial adjustment of the probe tip relative to the end of the guiding tube, in which case a measuring scale (not illustrated) is provided on the handpiece for reading the extent of adjustment. This measuring scale is referred to an initial position of the coupler sleeve 17 or an initial position of the probe tip 2' relative to the guiding tube 5 and calibrated for the measure of axial probe tip adjustment.

In the alternative embodiment illustrated in FIG. 3 a coupler sleeve 22 is employed which is equally screwed onto a connecting element 14, with interposition of a sealing ring 18. By contrast to the previous embodiment, the coupler sleeve 22 is here axially attached to the lithotripter handpiece 3 directly and may be clamped onto the handpiece by means of a damping screw cap 23 which is screwed onto a male thread 24 on the fastening end of the clamping sleeve. When the clamping cap 23 is unscrewed the coupler sleeve 22 may here hence be adjusted relative to the handpiece 3 and thus relative to the probe 2 so as to vary again the measure of axial adjustment of the probe tip 2' relative to the end of the guiding tube 5. The axial adjustment of the coupler sleeve 22 relative to the handpiece 3 is equally carried out along a measuring scale (not illustrated) which is provided on the handpiece 3 and calibrated in the aforementioned manner for the measure of adjustment of the probe tip 2' relative to an initial position.

We claim:

1. A device for removal of calculi including nephroliths, ureteroliths or urinary calculi, using a suction pump having a pump tube, an intracorporeal lithotripter, and an endoscope having an operating passage, the device comprising:

a probe of the intracorporeal lithotriper which transmits shock waves and which is inserted into the operating passage of the endoscope for lithotripsy in situ;

a guiding tube having an external diameter and an internal diameter where said external diameter is dimensioned for insertion of said guiding tube into the operating passage of the endoscope and said internal diameter is dimensioned for receiving said probe of the intracorporeal lithotripter;

said guiding tube and said probe forming a suction passage as an annular passage between said guiding tube and said probe when said probe is inserted into said guiding tube, said guiding tube having a first connecting bore connected to said suction passage;

a first Luer lock connector, coupled to said first connecting bore, for coupling the pump tube of the suction pump, the suction pump producing a suction pressure in said suction passage when the suction pump is coupled to said first Luer lock connector;

an adjustable shut-off means, coupled to said first connecting bore, for adjusting and shutting off the suction pressure produced by the suction pump when the suction pump is coupled to said first Luer lock connector; and a coupler means for mounting said guiding tube on the intracorporeal lithotripter.

2. The device according to claim 1, wherein said adjustable shut-off device is a trumpet-type valve comprising:

a valve housing; and a valve member having an interconnecting bore connecting said first connecting bore and said first Luer lock connector, said valve member being adjustably disposed in said valve housing, wherein adjustment of said valve member variably opens and closes the interconnecting bore to adjust and shut off said suction pressure when the suction pump is coupled to said first Luer lock connector.

3. A device according to claim 1, wherein:

said guiding tube further comprises a connecting element having a hollow screw fitting and a through-bore; and said coupler means comprises an interconnecting element which is screwed onto said hollow screw fitting, said interconnecting element having a second connecting bore which is axially aligned with said through-bore of said connecting element for interconnection with said suction passage, said second connecting bore being provided with a second Luer lock connector for connection of the tube of the suction pump when said probe of the intracorporeal lithotripter is removed from the guiding tube and said first connecting bore is shut off by said adjustable shut-off means.

4. A device according to claim 3, wherein the device further comprises a coupler sleeve which is coupled to the intracorporeal lithotripter and wherein said interconnecting element further comprises an extension having an outer thread for being screwed onto the coupler sleeve.

5. A device according to claim 4, wherein said coupler sleeve has a sealing washer which is fixed by cooperation of said coupler sleeve and said interconnecting element, said sealing washer sealing said suction passage of said guiding tube against said probe of the intracorporeal lithotripter as said probe is passed through said sealing washer.

6. A device according to claim 1, wherein said coupler means is axially adjustable for adjusting said probe of the intracorporeal lithotripter relative to said guiding tube when the probe is received therein.

7. A device according to claim 6, wherein said coupler means has a coupler sleeve and the intracorporeal lithotripter has a threaded sleeve having an actuator threading, said threaded sleeve being rotatably arranged with respect to the intracorporeal lithotripter, said coupler sleeve being adapted to engage said actuator threading so that by rotating said threaded sleeve relative to said coupler sleeve said probe of the intracorporeal lithotripter is axially adjusted relative to said guiding tube.

8. A device according to claim 6, wherein said coupler means has a coupler sleeve for (1) receiving the intracorporeal lithotripter and (2) allowing the intracorporeal lithotripter to be axially displaceable, said coupler sleeve comprising an outer thread and a clamping screw cap, said clamping screw cap engaging the outer thread for clamping said coupling sleeve to the intracorporeal lithotripter.

9. A device according to claim 1, wherein the guiding tube has an open end and adapted to hold a calculus to be fragmented in the open end of the guiding tube when the suction pump produces the suction pressure in said suction passage.

* * * * *

UNITED STATES PATENT AND TRADEMARK OFFICE
CERTIFICATE OF CORRECTION

PATENT NO. : 5,722,980

DATED : Mar. 3, 1998

INVENTOR(S) : Schulz et al.

It is certified that error appears in the above-identified patent and that said Letters Patent is hereby corrected as shown below:

On the title page:
FOREIGN PATENT DOCUMENTS shoule read as follows:

| | | |
|---|---|---|
| 0317507B1 | 5/1989 | European Pat. Off. |
| 3720424C2 | 12/1987 | Germany |
| 2268883 | 1/1994 | United Kingdom |
| WO93/08750 | 5/1993 | WIPO |
| 3545176C2 | 7/1987 | Germany |

Signed and Sealed this

Twenty-eighth Day of July, 1998

Attest:

BRUCE LEHMAN

*Attesting Officer*     *Commissioner of Patents and Trademarks*